(12) United States Patent
Wang et al.

(10) Patent No.: US 8,293,219 B2
(45) Date of Patent: Oct. 23, 2012

(54) USE OF LONG CARBON CHAIN QUATERNARY AMMONIUM SALT PHOSPHORIC ACID ESTER AS CONDITIONER FOR HAIR

(75) Inventors: Changguo Wang, Nanjing (CN); Evelyn Su, Nanjing (CN)

(73) Assignee: Nanjing Huashi Chemical Co., Ltd, Nanjing, Jiangsu (CN)

( * ) Notice: Subject to any disclaimer, the term of this patent is extended or adjusted under 35 U.S.C. 154(b) by 131 days.

(21) Appl. No.: 12/734,405

(22) PCT Filed: Oct. 30, 2007

(86) PCT No.: PCT/CN2007/003092
§ 371 (c)(1),
(2), (4) Date: Apr. 29, 2010

(87) PCT Pub. No.: WO2009/055963
PCT Pub. Date: May 7, 2009

(65) Prior Publication Data
US 2010/0254931 A1    Oct. 7, 2010

(51) Int. Cl.
*A61K 8/55* (2006.01)
*A61Q 5/12* (2006.01)
(52) U.S. Cl. ..................... 424/70.28; 558/170
(58) Field of Classification Search .......... None
See application file for complete search history.

(56) References Cited

U.S. PATENT DOCUMENTS

| 4,243,602 A | 1/1981 | O'Lenick, Jr. et al. |
| 4,283,542 A | 8/1981 | O'Lenick, Jr. et al. |
| 5,286,719 A | 2/1994 | Fost et al. |
| 6,451,775 B1 | 9/2002 | Smith et al. |
| 2004/0133996 A1 * | 7/2004 | Wolff et al. ............... 8/405 |

FOREIGN PATENT DOCUMENTS

JP    2004149462    *    5/2004

OTHER PUBLICATIONS

Phospholipids—A Natural Choice for Personal Care. Uniquema personal care. Business Briefing: Global Cosmetics Manufacturing 2004.*

* cited by examiner

*Primary Examiner* — Robert A Wax
*Assistant Examiner* — Danah Al-Awadi
(74) *Attorney, Agent, or Firm* — Hudak, Shunk & Farine Co. LPA

(57) ABSTRACT

Use of long carbon chain quaternary ammonium salt phosphoric acid ester of formula (I) as conditioner for hair.

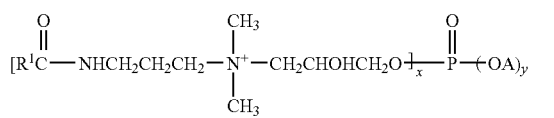

7 Claims, No Drawings

USE OF LONG CARBON CHAIN QUATERNARY AMMONIUM SALT PHOSPHORIC ACID ESTER AS CONDITIONER FOR HAIR

FIELD OF THE INVENTION

This invention relates to an use of long carbon chain quaternary ammonium phosphate ester, particularly the use of long carbon chain quaternary ammonium phosphate ester as a conditioner for hair.

TECHNICAL BACKGROUND OF THE INVENTION

Long carbon chain quaternary ammonium salt is a cation surfactant which has been widely applied as a shampoo conditioner in hair cosmetics. Long carbon chain quaternary ammonium salt can reduce electrostatic accumulation, maintain hair smoothness and improve hair combability. However, long carbon chain quaternary ammonium salt has apparent demerit, such as strong irritation, poor compatibility with anions, which limit its applications. The reason for wide use of long carbon chain quaternary ammonium salt lies in that the quaternary ammonium salt in its structure has positively charged nitrogen atoms, which function as electrostatic resistant. Additionally, long carbon chains such as fatty acid chains, polymer chains and the like have good affinity and thus can be attached to hair after washing. Therefore, long carbon chain quaternary ammonium salt exhibits the advantages of good dry combability, wet combability, electrostatic resistance as well as twist resistance. The length of the carbon chain would affect the performance of long carbon chain quaternary ammonium salt to a great extent. Longer carbon chain would provide more excellent performance and its affinity with the hair would be stronger. Meanwhile, the longer the carbon chain, the lower and milder the toxicity of its cells. However, quaternary ammonium salt would deposit when combining with anions, making the formula unstable. In order to reduce accumulation of the electric charges and make quaternary ammonium more compatible with anions, it is generally required to improve its structure, for example, to connect an EO (ethylene oxide) or a PO (propylene oxide) chain thereto. Another option is to modify its structure such as make it into an ampholytic surfactant, while this option would deteriorate the performance of quaternary ammonium salt.

Alkyl phosphate ester is a mild anion surfactant and has widely been applied in cleansing products such as cleansing facial milk, shower bath and the like.

The long carbon chain quaternary ammonium phosphate ester obtained by connecting the two structures described above is a special ampholytic surfactant having both structures of quaternary ammonium salt and phosphate ester. In addition to exhibiting surface activities of an ampholytic surfactant, said long carbon chain quaternary ammonium phosphate ester exhibits some other special properties, such as bacteriostasis. U.S. Pat. Nos. 4,243,602, 4,283,542 and 5,286,719 disclose methods for synthesizing the long carbon chain quaternary ammonium phosphate ester, its use as an antibacterial agent, and call it a biomimetic phospholipid.

The uses of long carbon chain quaternary ammonium phosphate ester as a surfactant in personal care and household products are widely disclosed in prior art. However, due to existence of the structure of phosphate ester, which is generally thought as affecting the conditioning properties of quaternary ammonium salt, the use of long carbon chain quaternary ammonium phosphate ester as a hair conditioner or a hair care agent has not been disclosed. Let alone the properties and use of the quaternary ammonium phosphate ester having an extremely long carbon chain structure

SUMMARY OF THE INVENTION

A purpose of this invention is to provide a new use of long carbon chain quaternary ammonium phosphate ester. Specifically, to provide an use of long carbon chain quaternary ammonium phosphate ester as a hair conditioner. The present invention can be used in shampoo, hair conditioner as well as products for improving hair quality.

The technical solution of this invention is:

Use of long carbon chain quaternary ammonium phosphate ester having formula (I) as a hair conditioner,

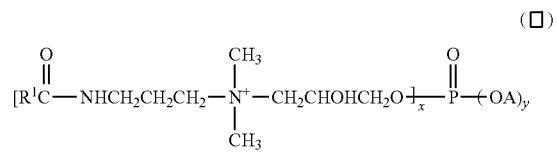

wherein, $R^1$=alkyl, alkoxyl-alkyl or one or more C/C double bond and/or triple bond substituted alkyl, alkoxyl-alkyl, or alkyl phenyl, alkoxyl phenyl, phenyl alkyl or phenyl alkoxyl alkyl, having the number of carbon atoms of 11~40;

A is H, Na, K, Li, $NH_4$, $NH_2CH_3$, $NH(CH_3)_2$, $NH_2CH_2CH_3$ or $NH(CH_2CH_3)_2$;

x=1 or 2, y=1 or 2, and x+y=3.

The long carbon chain quaternary ammonium phosphate ester is commercially available, or can be prepared by the methods known in the art. Long carbon chain quaternary ammonium phosphate esters having the number of $R^1$ carbon atoms less than 18 can be purchased directly from the market, other long carbon chain quaternary ammonium phosphate esters can be prepared by the methods known in the art, in which an amidated intermediate is prepared by long chain carboxylic acid and dimethyl propylene diamine, then the intermediate is reacted with quaternary ammonium compound reagent to obtain the long carbon chain quaternary ammonium phosphate ester. Said quaternary ammonium compound reagent can be prepared by the reaction of phosphoric acid or its salt with epoxy chloropropane.

Said long carbon chain quaternary ammonium phosphate ester compounds include but are not limited to the following: mono(di)-cocamidopropyl PG-dimonium chloride phosphate, mono(di)-palmitamidopropyl PG-dimonium chloride phosphate, mono(di)-stearamidopropyl PG-dimonium chloride phosphate, mono(di)-linoleamidopropyl PG-dimonium chloride phosphate, mono(di)-lenoamidopropyl PG-dimonium chloride phosphate, mono(di)-iso-hexadecanamidopropyl PG-dimonium chloride phosphate, mono(di)-isostearamidopropyl PG-dimonium chloride phosphate, mono (di)-erucamidopropyl PG-dimonium chloride phosphate, mono(di)-behenamidopropyl PG-dimonium chloride phosphate, mono(di)-cetyl polyoxyethylene acetamidopropyl PG-dimonium chloride phosphate, mono(di)-octadecyl polyoxyethylene acetamidopropyl PG-dimonium chloride phosphate, mono(di)-dodecyl benzamidopropyl PG-dimonium chloride phosphate, mono(di)-benzyl dodecanamidopropyl PG-dimonium chloride phosphate, mono(di)-benzyloxy dodecanamidopropyl PG-dimonium chloride phosphate, and the like.

Long carbon chain quaternary ammonium salts already known in the art have better dry and wet combability, electrostatic and twist resistance since the quaternary ammonium salts have positively charged nitrogen atoms, which are electrostatic resistant, Long carbon chain structure has good affinity with hair. However, as to quaternary ammonium phosphate ester ampholytic surfactant, although it has better compatibility with anion, the conditioning performance of quaternary ammonium would be affected due to less accumulation of electric charges.

The long carbon chain quaternary ammonium phosphate esters of the present invention show very good conditioning effect due to their unique structures screened by the inventor.

The long carbon chain quaternary ammonium phosphate esters of the present invention use long carbon chain as the oleophylic end of the surfactant and this structure enables the quaternary ammonium phosphate ester as a conditioner. Its substituting group $R^1$ contains a long carbon chain having 11-40 carbon atoms, preferably having greater than 18 carbon atoms, and more preferably having greater than 20 carbon atoms.

Said substituting group $R^1$ can be an aliphatic chain including linear chain or branched chain, saturated chain or carbon chain containing double bond or triple bond, or the alkoxyl-alkyl containing O atoms in the carbon chain, wherein the alkyl group is substituted by one or more C/C double bond and/or triple bond; said aliohatic chain may come from a fatty acid containing $R^1$, for example, $R^1$ is heptadecyl when it comes from stearic acid; and it is the same for other substituting group $R^1$. Said fatty acids include but is not limited to stearic acid, linoleic acid, isostearic acid, linolenic acid, isostearic acid, linoleic acid, erucic acid, docosanoic acid, octadecyl polyoxyethylene carboxylic acid and the like, and isostearic acid, erucic acid and docosanoic acid are preferred; the substituting group $R^1$ can also be alkyl phenyl, alkoxyl phenyl, phenyl alkyl, phenyl alkoxyl alkyl, such as dodecyl benzyl, benzyl dodecyl, benzyloxy dodecyl; the above-mentioned substituting groups $R^1$ containing aromatic groups can also come from their corresponding carboxylic acids. The carboxylic acid containing substituting group $R^1$ is taken to react with dimethyl propylene diamine to prepare amide intermediates, and then is subjected to quaternary ammoniation to obtain the long carbon chain quaternary ammonium salt phosphate ester of the present invention.

Typical phosphate surfactants are alkyl phosphates, such as monoalkyl, di-alkyl or tri-alkyl phosphates which exhibit unique mildness and are generally used in cleansing facial milk or shower gel. Phosphoric acids have buffer effect and can significantly alleviate the irritatant effects of acid and alkali. Said phosphoric acid and amine intermediate are connected by using propylene glycol to generate a quaternary ammonium structure, the resulting compound, i.e. long carbon chain quaternary ammonium phosphate ester thus has good conditioning performance, mildness and formula compatibility.

The effect of a hair conditioner is represented by its binding property with hair or functions due to its deposition on hair. After hair is washed with the conditioner, it is easy to unfasten and comb when it is twisted in wet state, and the hair exhibits gloss, smoothness and combability when dry. These are the effects of the conditioner. Many methods for testing the performance of the conditioner can be used but physical properties test and sensory evaluation are often used to test the combability, smoothness and gloss of the hair after washing with the hair conditioner.

Carding Force Test

Some hair of the oriental having a length of about 15 cm was taken, cleaned thoroughly with 1% SLS, rinsed with water for 2 minutes; the remaining water on the hair was then removed and the hair was immersed in a 10% sample formula at room temperature for 20 minutes. Then, the hair was taken out and rinsed with water for 2 minutes; after being dried in the air, the hair was tested by using Instron 3343 biomechanics tester and compared with the contrast sample. For the test results, see Table 1.

TABLE 1

Test of carding force

| Sample | Reduction of carding force |
| --- | --- |
| Blank contrast sample | 0 |
| 1% PFA | 5.8. |
| 1% BFA | 14.0 |
| 1% ISFA | 11.0 |
| 1% SFA | 7.0 |
| 0.2% PQ-10 + 2% silicone oil | 7.5 |
| 0.2% PQ-10 + 2% silicone oil + 1% BFA | 22.1 |

Wherein:
PFA mono-Palmitamidopropyl PG-dimonium chloride phosphate
BFA mono-Behenamidopropyl PG-dimonium chloride phosphate
ISFA mono-Isostearamidopropyl PG-dimonium chloride phosphate
SFA mono-Stearamidopropyl PG-dimonium chloride phosphate
PQ-10 Polyquaternary ammonium salt-10

Greater reduction of carding force shows that the hair is easier to comb and the combability of the conditioner used has better performance. The long chain quaternary ammonium phosphate ester showed good combability performance; and the quaternary ammonium phosphate ester having substituting group $R^1$ with more carbon atoms showed much better combability performance; the quaternary ammonium phosphate ester having branched chain structure $R^1$ had better combability performance than normal chain.

Test of Gloss, Smoothness and Moisture Preservation Properties

The hair treatment process was the same with carding force test. The gloss, smoothness and moisture preservation performance of the hair were evaluated after using the conditioner. The evaluation was made by 5 professional personnel according to their sensory judgment. For the test results, see Table 2.

TABLE 2

Test of gloss, smoothness and moisture preservation properties

| Sample | Gloss | Smoothness | Moisture preservation |
| --- | --- | --- | --- |
| Blank contrast sample | 1 | 1 | 1 |
| 1% PFA | 3 | 2 | 3 |
| 1% BFA | 4 | 5 | 5 |
| 1% ISFA | 3 | 5 | 4 |
| 1% SFA | 3 | 3 | 3 |
| 0.2% PQ-10 + 2% silicone oil | 5 | 4 | 5 |
| 0.2% PQ-10 + 2% silicone oil + 1% BFA | 5 | 5 | 5 |

The values for respective properties were categorized into five scores 1-5, from low to high. The numeric values shown in the table were the average of the scores given by five evaluators.

In respect of gloss property, the respective value of long chain quaternary ammonium phosphate ester was slightly lower than the formulas containing silicone oil and PQ-10.

However, in respect of smoothness and moisture preservation, the former showed much better performance.

The above tests indicated that the long chain quaternary ammonium phosphate ester of this invention shows very good combability, smoothness and gloss properties and thus can be used as hair conditioner in shampoo as well as other products for improving hair quality.

The appropriate amount of conditioner deposited on hair is important. Too less amount of the conditioner deposited on hair would have less conditioning effect; whereas too much amount would result in massiveness, dryness and unfreshness after using the conditioner. Appropriate amount of conditioner should be used in order to satisfy the requirements of the formula for different products.

Long carbon chain quaternary ammonium phosphate ester can be applied in hair washing products, the amount is 0.01-15% (w/w, the same below), preferably, the amount is 0.1-10%, more preferably, the amount is 0.3-5%. It can also be used in hair care products, the amount is 0.05-20%, preferably, the amount is 0.2-10%, more preferably, the amount is 0.5-5%.

As the hair conditioner, when long carbon quaternary ammonium phosphate ester is used in hair washing products or hair care products, the products can be made into liquid product or paste product. According to the need of product formula, like various already known hair conditioners, long carbon chain quaternary ammonium phosphate ester can be used in water and/or various organic solvents, and can be made into products by further adding therein with additives such as surfactant, thickener, pH adjusting agent, preservative, softener, aromatic and/or spice and the like.

The long carbon chain quaternary ammonium phosphate ester described in this invention is mild and of good conditioning effect and formula compatibility. It can be used as hair conditioner in hair washing products or hair care products to make hair easy to comb, electrostatic resistant, twist resistant and improve the sense after washing.

The present invention will be further described by examples below. However, the scope of the present invention shall not be limited to these examples. Unless otherwise specified, the amount is based on weight by parts for the formula containing long carbon chain quaternary ammonium phosphate ester described below.

EXAMPLES

Example 1

Preparation of mono-behenamidopropyl PG-dimonium chloride phosphate 162 g of docosanoic acid was placed into a reaction flask, the temperature was heated to 120□, 66 g of N,N-Dimethyl-1,3-propanediamine was titrited therein. Then, the temperature was slowly raised to 160□-170□ and maintained at this level until the amine value was smaller than 5 mgKOH/g. Next, the temperature was cooled to 100□, and 160 g of 50% aqueous solution of chloropropylene glycol sodium phosphate and 450 g of water were added into the reaction flask; the temperature was maintained at 90□-95□ for reacting for 3 hours before cooled to normal temperature. The reaction product was subjected to suction filtration with a Buchner funnel and dried in a oven for four hours at 60□-65□ to get the solid product.

Example 2

Preparation of mono-isostearamidopropyl PG-dimonium chloride phosphate 135 g of isostearic acid was placed into a reaction flask, the temperature was heated to 120□, 66 g of N,N-Dimethyl-1,3-propanediamine was titrited therein. Then, the temperature was slowly raised to 150□ and maintained at this level until the amine value was smaller than 10 mgKOH/g. Next, the temperature was cooled to 100□, and 160 g of 50% aqueous solution of chloropropylene glycol sodium phosphate and 450 g of water were added into the reaction flask; the temperature was maintained at 90□-95□ for reacting for 3 hours before cooled to normal temperature to get the product having a concentration of 30%.

Example 3

The formula of shampoo containing long carbon chain quaternary ammonium phosphate ester is as follows:

| Phase A | |
|---|---|
| Deionized water | 35.0 |
| Sodium edetate | 0.05 |
| Guar hydroxypropyl trimonium chloride | 0.20 |
| Hydroxypropyl guar gum | 0.20 |
| Linoleamidopropyl PG-dimonium chloride phosphate | 0.50 |
| Sodium lauryl ether sulfate | 25.00 |
| Sodium cocoamphoacetate | 10.0 |
| Oocoamide propyl betaine | 5.0 |
| Cocofatty acid diethanolamide | 2.00 |
| Distearin | 1.00 |
| Phase B | |
| Anhydrous citric acid | 0.15 |
| Dimethyl polysiloxane | 1.34 |
| Actiplex 167 (glycerin extraction from plant) | 0.20 |
| Preservative | q.s. |
| Spice | q.s. |
| Phase C | |
| KCl (Reheis) | 0.73 |
| Deionized water | ~100 |

Under agitation, phase A was added and heated to 80□. Then cooled to 40□ and phase B and C were added therein sequentially; keep agitation until the system was homogeneous.

Example 4

The formula of shampoo containing long carbon chain quaternary ammonium phosphate ester is as follows:

| Phase A | | | |
|---|---|---|---|
| Ammonium lauryl ether sulphate | 14.0 | Dodecyl sulfate ammonium | 6.0 |
| Cocamide MEA | 1.0 | Disodium cocoamphodipropionate | 3.0 |
| Glyceryl distearate | 2.0 | Hexadecanol and octadecanol | 0.4 |
| Citric acid | 0.3 | EDTA disodium | 0.1 |
| Sodium chloride | 0.5 | Water | 38.2 |
| Phase B | | | |
| BFA | 1.0 | Deionized water | 20.0 |
| Phase C | | | |
| Polyquaternary ammonium salt-10 | 0.2 | Water | 10.0 |
| Phase D | | | |
| Polydimethyl siloxane (DC-7137) | 1.5 | Polydimethyl siloxane (DC-1785) | 1.0 |

| | | | |
|---|---|---|---|
| Polyquaternary ammonium salt-47 | 1.0 | Preservative | 0.3 |
| Spice | 0.5 | | |

The ammonium lauryl ether sulphate, ammonium lauryl sulfate and deionized water of phase A were heated to 75☐ and agitated to dissolve them, then other ingredients of phase A were added and agitated until they dissolve. Next, phase B and C were added into phase A after respectively heating them to dissolve, the solution obtained was cooled to 40☐ and then other ingredients of phase D were added.

Example 5

The shampoo containing long carbon chain quaternary ammonium phosphate ester had the same formula as example 4, the difference was that BFA of phase B was substituted by ISFA.

Example 6

The shampoo containing long carbon chain quaternary ammonium phosphate ester had the same formula as example 4, the difference was that BFA of phase B was substituted by PFA.

Example 7

The shampoo containing long carbon chain quaternary ammonium phosphate ester had the same formula as example 4, the difference was that BFA of phase B was substituted by mono-erucamidopropyl PG-dimonium chloride phosphate.

Example 8

The shampoo containing long carbon chain quaternary ammonium phosphate ester has the same formula as example 4, the difference was that BFA of phase B was substituted by mono-octadecyl polyoxyethylene acetamidopropyl PG-dimonium chloride phosphate.

Example 9

The shampoo containing long carbon chain quaternary ammonium phosphate ester had the same formula as example 4, the difference was that BFA of phase B was substituted by mono-dodecyl benzamidopropyl PG-dimonium chloride phosphate.

Example 10

The shampoo containing long carbon chain quaternary ammonium phosphate ester had the same formula as example 4, the difference was that BFA of phase B was substituted by mono-benzyl dodecanamidopropyl PG-dimonium chloride phosphate.

Example 11

The shampoo containing long carbon chain quaternary ammonium phosphate had the same formula as example 4, the difference was that BFA of phase B was substituted by mono-benzyloxy dodecanamidopropyl PG-dimonium chloride phosphate.

Example 12

The formula of hair conditioner containing long carbon chain quaternary ammonium phosphate ester is as follows:

| | |
|---|---|
| Methyl glucoside ether-20 | 5.00 |
| Dimethyl silicone | 2.0 |
| Hydroxyethyl cellulose | 0.5 |
| Hexadecanol | 1.0 |
| ISFA | 2.0 |
| Propylene glycol | 50.0 |
| Preservative | 0.5 |
| Spice | 0.5 |
| Deionized water | ~100 |

Example 13

The hair conditioner containing long carbon chain quaternary ammonium phosphate had the same formula as example 12, the difference was that ISFA was substituted by mono-erucamidopropyl PG-dimonium chloride phosphate.

Example 14

The hair conditioner containing long carbon chain quaternary ammonium phosphate ester had the same formula as example 12, the difference was that ISFA was substituted by mono-lauramidopropyl PG-dimonium chloride phosphate.

Example 15

The hair conditioner containing long carbon chain quaternary ammonium phosphate ester had the same formula as example 12, the difference was that ISFA was substituted by mono-palmitamidopropyl PG-dimonium chloride phosphate.

Example 16

The hair conditioner containing long carbon chain quaternary ammonium phosphate ester had the same formula as example 12, the difference was that ISFA was substituted by mono-lenoamidopropyl PG-dimonium chloride phosphate.

Example 17

The shampoo containing long carbon chain quaternary ammonium phosphate ester had the same formula as example 12, the difference was that ISFA was substituted by SFA.

What is claimed is:
1. A process for conditioning hair, comprising the steps of:
preparing a long carbon chain quaternary ammonium phosphate ester having formula (I):

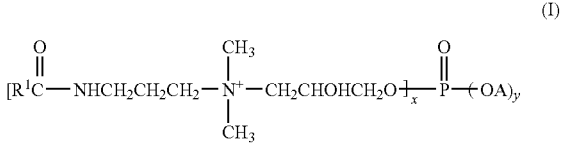

wherein, $R^1$=alkyl, alkoxyl-alkyl or one or more C/C double bond and/or triple bond substituted alkyl, alkoxyl-alkyl, or alkyl phenyl, alkoxyl phenyl, phenyl alkyl or phenyl alkoxyl alkyl, having the number of carbon atoms of 21~40;

A is H, Na, K, Li, $NH_4$, $NH_2CH_3$, $NH(CH_3)_2$, $NH_2CH_2CH_3$ or $NH(CH_2CH_3)_2$;

x=1 or 2, y=1 or 2, and x+y=3, and applying said quaternary ammonium phosphate ester to hair.

2. The process of claim 1, wherein said $R^1$ is derived from erucic acid, docosanoic acid and octadecyl polyoxyethylene acetic acid.

3. The process of claim 1, wherein said $R^1$ is derived from dodecyl benzoic acid, benzyl dodecyl acid or benzyloxy dodecyl acid.

4. The process of claim 1, wherein said long carbon chain quaternary ammonium phosphate ester is contained in a hair washing product or in a hair care product.

5. The process of claim 4, wherein the amount of said long carbon chain quaternary ammonium phosphate ester in the hair washing product is 0.01-15% by weight of the total hair washing product.

6. The process of claim 4, wherein the amount of said long carbon chain quaternary ammonium phosphate ester in the hair care product is 0.05-20% by weight of the total hair care product.

7. A process for conditioning hair, comprising the steps of:
preparing a long carbon chain quaternary ammonium phosphate ester having the formula (I):

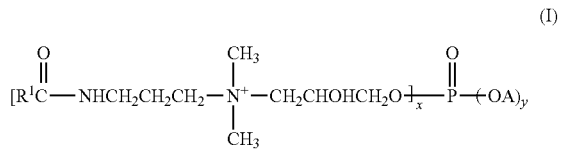

wherein $R^1$ is derived from isostearic acid;

A is H, Na, K, Li, $NH_4$, $NH_2CH_3$, $NH(CH_3)_2$, $NH_2CH_2CH_3$ or $NH(CH_2CH_3)_2$;

x=1 or 2, y=1 or 2, and x+y=3, and applying said quaternary ammonium phosphate ester to hair.

* * * * *